United States Patent [19]

Imaki et al.

[11] 4,336,453
[45] Jun. 22, 1982

[54] NON-DISPERSION TYPE INFRARED ANALYZER FOR SIMULTANEOUSLY DETERMINING PLURAL COMPONENTS

[75] Inventors: Takao Imaki; Hajime Mikasa; Niro Sakai, all of Miyanohigashi, Japan

[73] Assignee: Horiba Limited, Kyoto, Japan

[21] Appl. No.: 170,879

[22] Filed: Jul. 21, 1980

[30] Foreign Application Priority Data

Jul. 20, 1979 [JP] Japan .................................. 54-92829

[51] Int. Cl.³ .............................................. G01J 1/00
[52] U.S. Cl. .................................................. 250/344
[58] Field of Search ............... 250/343, 344, 345, 373; 356/437

[56] References Cited

U.S. PATENT DOCUMENTS 3,898,462  8/1975  Ishida et al. ......................... 250/344
4,180,733  12/1979  Ueda .................................... 250/345
4,232,223  11/1980  Onishi et al. ........................ 250/345
4,256,964  3/1981  Ishida et al. ......................... 250/345

Primary Examiner—Alfred E. Smith
Assistant Examiner—Janice A. Howell
Attorney, Agent, or Firm—Wenderoth, Lind & Ponack

[57] ABSTRACT

A non-dispersion type infrared analyzer for simultaneously determining plural components of a sample fluid, wherein a standard fluid and a sample fluid are alternately supplied in a cell and a plurality of pneumatic detectors, each of which corresponds respectively to one component to be determined, are arranged optically in series with respect to a light source. The extremely troublesome zero-adjustment, adjustment of the phases and re-adjustment of the compensation for eliminating the influences of interference components due to changes in the zero-drift or the deviation of phases are not required.

3 Claims, 4 Drawing Figures

NON-DISPERSION TYPE INFRARED ANALYZER FOR SIMULTANEOUSLY DETERMINING PLURAL COMPONENTS

BACKGROUND OF THE INVENTION

1. Field of the Invention

The present invention relates to a non-dispersion type infrared analyzer and in particular to an infrared analyzer which can simultaneously determine plural components in a fluid sample by means of only one analyzer.

2. Description of the Prior Art

The conventional method in which plural components are simultaneously determined by a single analyzer encounter more problems than the method in which only one component is determined by a single analyzer. For example, phase adjustments and optical adjustments are required when plural detectors are used. Also, a zero drift adjustment is required for each detector because drift causing factors such as a change in the light intensity, contaminants soiling the cells or the like cause different effects upon the different components to be determined. For example, in the conventional non-dispersion type infrared analyzer for determining plural components as shown in FIG. 1, the optical adjustment is carried out by locating screens 2 between detectors 1 and consequently a large space is required and the spatial losses are large Furthermore, the harmful effects of zero drift must be overcome by carefully carrying out the electrical adjustment of each detector 1. But, one adjustment is not enough and the time consuming troublesome adjustment is repeatedly required. Also, any slight deviation in the placement of the center of rotation of a chopper 3 leads to a deviation in the angle at which the blades of the chopper cut the two light paths 4, 5 and accordingly result a poor S/N ratio. As a result, in the case when a fluid sample has one high content component and one low content component, even though the high content component can be determined, the other low content component cannot be determined unless the length of the cell is changed. As described above, the contents of components to be determined in a fluid sample are generally different and accordingly the above described analyzer has a serious problem that it can only be applied for the case in which the fluid sample has components to be determined having almost the same concentration. Conversely, the use of the above-described analyzer with the above-described usual fluid sample leads to significant differences in the sensitivity and accuracy of detectors 1, such differences resulting in a fatal defect with respect to the analyzer component determination. Furthermore, in the case when plural components are to be determined, it is necessary to compensate each output from each detector with the output of every other detector, as shown in the specification of U.S. Pat. No. 3,898,462, because the characteristic absorption bands of components to be determined may frequently overlap each other so as to interfere with each other. In addition, the adjustment of the above-described compensation must be repeated for every zero adjustment and adjustment of the phases and accordingly, the analyzer operation is unusually troublesome when a deviation occurs in the zero drift and phases.

SUMMARY OF THE INVENTION

It is an object of the present invention to provide a non-dispersion type infrared analyzer for simultaneously determining plural components which does not require the adjustment of the zero drift and phases, has an improved S/N ratio, and is able to determine plural components with a high sensitivity and high accuracy without changing the length of the cells, and requires no repeated readjustments of the compensation used for eliminating interferences due to deviations in the zero drift and phases, such repeated readjustments normally being required in the conventional analyzer. That is, a non-dispersion type infrared analyzer according to the present invention can completely overcome the above-described defects by adopting the "fluid-modulating method" in which the standard fluid (zero fluid or fluid of constant concentration) and the sample fluid are alternately supplied into the cell and by arranging pneumatic detectors, such as detectors of the condenser-microphone type or microflow-sensor type, in correspondence with the components to be determined and in series optically with respect to the source of light.

DESCRIPTION OF THE PREFERRED EMBODIMENTS

Figure 1:
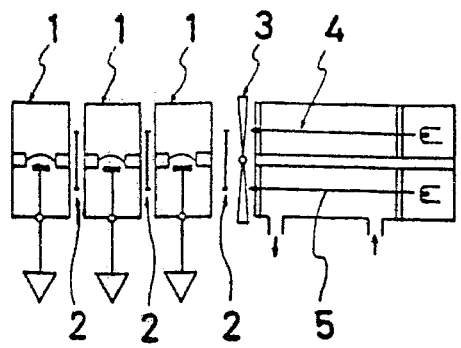
FIG. 1 shows the construction of a conventional non-dispersion type infrared analyzer for determining plural components simultaneously.
Figure 2:
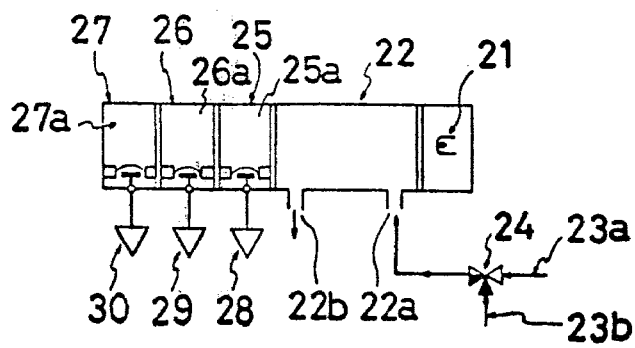
FIG. 2 shows the construction of a first embodiment of the present invention.

Two examples of a non-dispersion type infrared analyzer according to the present invention will be described hereinafter referring to FIG. 2 and FIG. 3. FIG. 2 shows a non-dispersion single cell type infrared analyzer in which 21 designates a source of light for emitting infrared rays, 22 designating a sample cell provided with a fluid inlet 22a and a fluid outlet 22b, 23a designates a passage for supplying a sample fluid, (for example-a sample gas), 23b designates a passage for supplying a standard fluid such as zero gas or gas of a constant concentration (zero gas is used hereinafter), and 24 designates a passage change-over valve. A predetermined quantity of a sample gas and zero gas is alternately supplied into the sample cell 22 by periodically changing-over the passage change-over valve 24 to perform "fluid modulation". Numerical designations 25, 26 and 27 designate pneumatic detectors, for example-condenser-microphone type detectors, which are arranged in series optically with respect to the source of light 21 as shown in FIG. 2; each of the detectors respectively corresponding to the components to be determined. For example, detector 25 is used for the determination of CO, detector 26 is used for the determination of hydrocarbons, and detector 27 is used for the determination of NO. Consequently, the gaseous mixture consisting of the components to be determined and the zero gas at a predetermined partial pressure ratio are enclosed in light-receiving rooms 25a, 26a and 27a of the detectors. It is apparent to one skilled in the art that a "microflowsensor", which is based on the principle that the fluid flow due to the difference in pressure generated by the absorption of infrared rays by a gas contained within two chambers of a detector acting on heated wires (such as platinum wires) arranged between the two chambers of the detector results in a change in the electric resistance of the heated wires, may be used instead of a condenser-microphone type detector.

Figure 3:
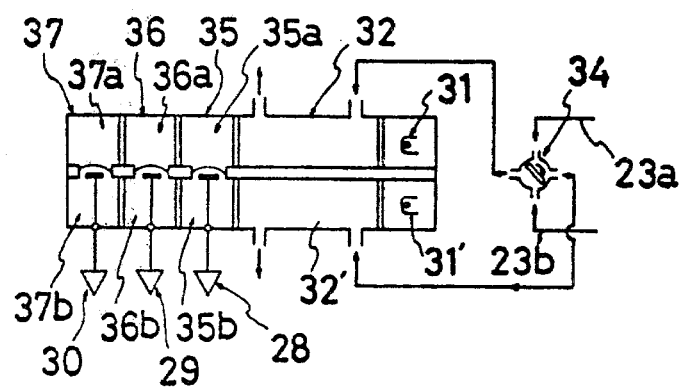
FIG. 3 shows the construction of a second embodiment of the present invention.

Numerical designations 28, 29 and 30 in FIGS. 2 and 3 designate amplifiers. The output from said amplifiers may be compensated, if necessary, to eliminate the interference as described hereinafter, (i.e.—if the components to be determined interfere with each other).

According to such a construction, the "fluid modulation" technique, in which a sample gas and zero gas are alternately supplied into said sample cell 22 by changing-over valve 24 results in infrared rays emitted from the source of light 21 being absorbed by the components to be determined in the sample cell 22 to obtain a "modulated" light ray which passes through the sample cell 22 (in the case when the sample gas is supplied) and passes through the sample cell 22 without being absorbed (in the case when the zero gas is supplied). Infrared rays enter in the light-receiving chambers 25a, 26a and 27a of the detectors which thereby generate signals corresponding to the concentrations of the components to be determined.

FIG. 3 shows a non-dispersion double cell type infrared analyzer. A non-dispersion double cell type infrared analyzer using the "fluid modulation" method has been described in copending U.S. application Ser. No. 972,485, filed Dec. 22, 1978 now U.S. Pat. No. 4,256,964 and having a common co-inventor with respect to the present application. FIG. 3 shows an example of such a non-dispersion double cell type of infrared analyzer using the "fluid modulation" method utilized in conjunction with the present invention. In FIG. 3, 23a designates a sample fluid-supplying passage, (for example-a passage for supplying sample gases), 23b designates a passage for supplying a standard fluid, (for example-a zero gas), 28, 29 and 30 designate amplifiers, 31 and 31' designate a pair of light sources, 32 and 32' designate a pair of cells, and 35, 36 and 37 designate pneumatic detectors, (for example-detectors of a condenser-microphone type), corresponding to the components to be determined (CO, hydrocarbons and NO in the present example). Detectors 35, 36 and 37 each have two light-receiving chambers 35a, 35b; 36a, 36b and 37a, 37b, respectively, in which a gaseous mixture consisting of the components to be determined corresponding thereto and a zero base gas is enclosed. For example, the gaseous mixture consisting of CO and a zero gas is enclosed in the light-receiving chambers 35a, 35b. Furthermore, as shown in FIG. 3, the light-receiving chambers 35a, 36a and 37a are arranged optically in series with respect to the light source 31, the light-receiving chambers 35b, 36b and 37b being arranged optically in series with respect to the light source 31'. Numerical designation 34 designates a passage change-over valve which simultaneously supplies a sample gas into one cell 32 (or 32') and a zero gas into another cell 32' (or 32) to supply alternately and periodically a sample gas and a zero gas of a predetermined quantity into cells 32, 32'.

Figure 4:
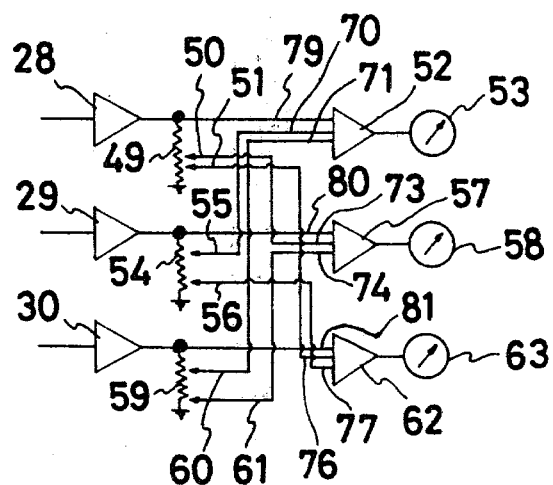
FIG. 4 is a circuit showing an embodiment of the present invention in which a circuit for carrying out the compensation used for eliminating the harmful effects of interference components is connected to each detector.

FIG. 4 shows a conventional circuit for carrying out the compensation of the outputs from the amplifiers (28, 29 and 30, as shown in FIG. 2 and FIG. 3) in order to eliminate the above-described interferences. In FIG. 4, 49, 54 and 59 designate output level setters (potentiometers) for compensating interferences; 70, 71, 73, 74, 76 and 77 designate interference signal input lines; 79, 80 and 81 designate conductors; 52, 57 and 62 designate adders; and 53, 58 and 63 designate indicators.

The output signal from amplifier 28 is fed to a voltage-divider 49, provided with adjusting taps 50, 51 and fed to the adder 52; the output signal from amplifier 29 is fed to a voltage-divider 54, provided with adjusting taps 55, 56, and fed to the adder 57; the output signal from amplifier 30 is fed to a voltage-divider 59, provided with adjusting taps 60, 61, and fed to the adder 62.

Each detector is adjusted so as to detect an output corresponding to the concentration of each component to be determined in said sample gas. The adjustment is carried out by passing the standard gas of a predetermined concentration prepared by diluting the equivalent mixture of CO, hydrocarbon and NO with $N_2$ gas through the cell as a sample gas and adjusting the positions of taps 50, 51, 55, 56, 60 and 61 so as to provide detector outputs corresponding to the predetermined concentrations of the components to be determined.

As described above, it is necessary for each detector to be preliminarily adjusted several times so as to detect an output corresponding to the concentration of CO gas, hydrocarbon gas and NO gas; the adjustments are made using the standard gas prepared by diluting said equivalent mixture of CO gas, hydrocarbon gas and NO gas with an inert gas. Although CO, hydrocarbon gas and NO gas show their principle absorption bands at 4.3, 3.5 and 5.3 microns, respectively, they have sub-absorption bands ("background") which interferes with the accurate determination of other gaseous substances contained in the sample gas. Unnecessarily high signal outputs are generated by the detectors due to such sub-absorption bands. Accordingly, the interference value due to each component is adjusted for each component in order to compensate for the interference value and such a value added to the primary output for each component to be compensated. For example, in the case of the determination of CO, the representative current signal of the sub-absorption bands for NO is received from variable tap 60 and subtractively added in adder 28 to the output signal generated by the detector of CO and provided by amplifier 28. In case of the determination of hydrocarbon, the representative current signal of the sub-absorption bands for NO is received from variable tap 61 and subtractively added in adder 57 to the output signal generated by amplifier 29 of said hydrocarbon detector. Similarly, the method applies to the case of the determination of CO. The total signals are indicated by indicators 53, 58 and 63.

In the present invention, the use of the "fluid-modulation method", in which a standard fluid and a sample fluid are alternately supplied into a cell and plural pneumatic detectors are optically arranged in series with respect to a light source, lead to the following special effects:

(a) While the low accuracy in the component determination due to zero-drift, span-drift and the deviation of phases is a serious problem in the above-described prior art analyzer, the adjustments made to compensate for zero-drift, span-drift and the deviation of phases have been extremely troublesome in such conventional analyzers because such zero-drift adjustments, adjustment of phases or the like must be performed for each of the plural detectors when zero-drift, deviation of phases or the like occurs. On the other hand, in the analyzer of the "fluid-modulating method" type in accordance with the present invention, zero-drift is not generated principally because such an analyzer is not influenced by drifting factors such as changes in the light intensity, contamination of a cell or the like. That is, the amount of energy entering into the detector from the light is changed by a portion that is absorbed by the sample fluid because the zero fluid and the sample fluid of a definite concentration are alternately passed through a cell in the "fluid-modulation method" type, the zero fluid and the sample fluid are alternately supplied into a cell and consequently the amount of energy transmitted from the light source to the detector is changed by the amount absorbed by the sample fluid. In the case when the zero fluid is passed through a cell or (cells) as the sample fluid, (that is to say, during zero-adjustment), namely, when the zero fluid is always being passed through a cell or (cells), a zero-drift is not generated because the energy input to the detector is not changed at all. That is, zero-drift does not occur. Furthermore, in the analyzer of the "fluid-modulation method" type in accordance with the present invention, a deviation of the phases does not occur because such an analyzer does not include a chopping mechanism used in a conventional analyzer of the chopping method type in which a deviation of the phases is inevitable due to the shaking of the chopper-axis, errors in manufacturing the chopper-blade with respect to its shape or the like.

As described above, an analyzer of the "fluid-modulation method" type does not have any zero-drift and deviations of the phases and accordingly, an analyzer according to the present invention has an advantage in that troublesome adjustments of the zero-point and the phases are not required for each detector but only the adjustment of the span is required. In a conventional analyzer used for determining plural components, all of the above-described adjustments are required.

(b) Furthermore, troublesome zero-adjustment, adjustment of phases and also the re-adjustment of the compensation caused by zero-drift or the deviation of phases must be repeated in the case when a conventional analyzer was provided with a compensation-circuit for eliminating the influences of interference components as shown in FIG. 4. In contradistinction, an analyzer according to the present invention has a significant advantage in that both the zero-drift and the deviation of phases do not occur and consequently, the extremely troublesome re-adjustment of the compensation due to zero-drift or the deviation of phases does not have to be repeated, even though the analyzer is provided with a compensation circuit for eliminating the influences of interference components.

(c) An analyzer according to the present invention can determine plural components of different concentrations and accordingly of different outputs by means of a cell having a single uniform length. In the case of the double cell "fluid-modulation method" type analyzer, as shown in FIG. 3, the output of the signal is doubled, as described in the specification of U.S. patent application Ser. No. 972,485, now U.S. Pat. No. 4,256,964 and consequently, an accurate determination can be achieved in spite of the single uniform cell length. A double cell type analyzer according to the present invention exhibits particularly advantageous characteristics.

(d) Furthermore, an analyzer according to the present invention has a compact construction which does not exhibit any spatial loss and does not exhibit a deterioration of the S/N ratio due to the shaking of the rotational axis of the chopper, because an analyzer according to the present invention does not require screening plates and a chopper, such elements being required in conventional analyzers.

What is claimed is:

1. A non-dispersion type infrared analyzer for simultaneously determining plural components of a sample fluid and comprising:

a light source;

a sample cell;

a plurality of pneumatic detectors arranged in a row adjacent said sample cell, wherein said light source provides light rays arranged to pass serially through said sample cell and said plurality of pneumatic detectors;

a first conduit for supplying said sample fluid;

a second conduit for supplying a standard fluid;

a fluid flow path change-over means connected to said first and second conduits and said sample cell for alternately supplying fixed amounts of said standard fluid and said sample fluid to said sample cell;

wherein each of said plurality of pneumatic detectors is arranged to respectively correspond to one of said plural components to be determined.

2. A non-dispersion type infrared analyzer according to claim 1, further comprising an electric circuit means electrically connected to said plurality of pneumatic detectors for processing electrical signals generated by said plurality of pneumatic detectors and for eliminating interference components of said electrical signals generated by said plurality of pneumatic detectors.

3. A non-dispersion type infrared analyzer for simultaneously determining plural components of a sample fluid and comprising:

a light source;

first and second sample cells arranged adjacent to each other;

a plurality of pneumatic detectors arranged adjacent said first and second sample cells, wherein said light source directs light rays simultaneously through said first and second sample cells and then serially through said plurality of pneumatic detectors;

a first conduit for supplying said sample fluid;

a second circuit for supplying a standard fluid;

fluid flow path change-over means connected to said first and second conduits and said first and second sample cells for alternately supplying said standard fluid and said sample fluid to said first and second sample cells, said fluid flow path change-over means supplying said sample fluid to said first cell and said standard fluid to said second cell simultaneously and supplying said standard fluid to said first cell and said sample fluid to said second cell simultaneously;

wherein each of said plurality of pneumatic detectors respectively corresponds to one of said plural components to be determined.

* * * * *